US009911984B2

United States Patent
Tamirisa et al.

(10) Patent No.: US 9,911,984 B2
(45) Date of Patent: *Mar. 6, 2018

(54) SEMI-SOLID ELECTROLYTES FOR BATTERIES

(71) Applicant: Medtronic, Inc., Minneapolis, MN (US)

(72) Inventors: Prabhakar A. Tamirisa, Brooklyn Park, MN (US); Jody J. Klaassen, Minneapolis, MN (US); Hui Ye, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 96 days.

This patent is subject to a terminal disclaimer.

(21) Appl. No.: 14/740,356

(22) Filed: Jun. 16, 2015

(65) Prior Publication Data
US 2015/0364773 A1    Dec. 17, 2015

Related U.S. Application Data

(60) Provisional application No. 62/013,188, filed on Jun. 17, 2014, provisional application No. 62/014,215, filed on Jun. 19, 2014.

(51) Int. Cl.
*H01M 6/18* (2006.01)
*H01M 10/052* (2010.01)
(Continued)

(52) U.S. Cl.
CPC ............ *H01M 6/187* (2013.01); *A61N 1/378* (2013.01); *H01M 10/052* (2013.01);
(Continued)

(58) Field of Classification Search
CPC .............. H01M 6/187; H01M 10/052; H01M 10/0656; H01M 10/0567; H01M 10/0568; H01M 10/0569; H01M 2/0207; H01M 2/20222; H01M 4/382; H01M 4/405; H01M 4/485; H01M 4/505; H01M 4/525; H01M 4/5815; H01M 4/5835; H01M 4/587;
(Continued)

(56) References Cited

U.S. PATENT DOCUMENTS 3,271,199 A    9/1966  Beste et al.
4,645,726 A    2/1987  Hiratani et al.
(Continued)

FOREIGN PATENT DOCUMENTS

CN    100470685    3/2009
CN    103035947    1/2013
(Continued)

OTHER PUBLICATIONS

Wang, Hui, et al., Interface Properties Between Lithium Metal and a Composite Polymer Electrolyte of PEO18Li (CF3SO2)2N-tetraethylene Glycol Dimethyl Ether, Membranes 2013, 3, pp. 298-310.
(Continued)

*Primary Examiner* — Gregg Cantelmo (57) ABSTRACT

Semi-solid electrolyte compositions are disclosed. The semi-solid electrolyte compositions contain a glyme or mixture of glymes, a lithium salt(s), and a polymeric complexing agent(s).

16 Claims, 8 Drawing Sheets

(51) Int. Cl.

| | | |
|---|---|---|
| *H01M 10/0565* | (2010.01) | |
| *H01M 10/0567* | (2010.01) | |
| *H01M 10/0568* | (2010.01) | |
| *H01M 10/0569* | (2010.01) | |
| *A61N 1/378* | (2006.01) | |
| *H01M 2/02* | (2006.01) | |
| *H01M 4/38* | (2006.01) | |
| *H01M 4/40* | (2006.01) | |
| *H01M 4/485* | (2010.01) | |
| *H01M 4/505* | (2010.01) | |
| *H01M 4/525* | (2010.01) | |
| *H01M 4/58* | (2010.01) | |
| *H01M 4/583* | (2010.01) | |
| *H01M 4/587* | (2010.01) | |

(52) U.S. Cl.
CPC ... *H01M 10/0565* (2013.01); *H01M 10/0567* (2013.01); *H01M 10/0568* (2013.01); *H01M 10/0569* (2013.01); *H01M 2/0207* (2013.01); *H01M 2/0222* (2013.01); *H01M 4/382* (2013.01); *H01M 4/405* (2013.01); *H01M 4/485* (2013.01); *H01M 4/505* (2013.01); *H01M 4/525* (2013.01); *H01M 4/587* (2013.01); *H01M 4/5815* (2013.01); *H01M 4/5835* (2013.01); *H01M 2220/30* (2013.01); *H01M 2300/0025* (2013.01); *H01M 2300/0085* (2013.01); *H01M 2300/0091* (2013.01)

(58) Field of Classification Search
CPC ..... H01M 2220/30; H01M 2300/0025; H01M 2300/0085; H01M 2300/009; A61N 1/378
See application file for complete search history.

(56) References Cited

U.S. PATENT DOCUMENTS

| | | | |
|---|---|---|---|
| 5,154,992 A | 10/1992 | Berberick et al. | |
| 5,223,353 A | 6/1993 | Ohsawa et al. | |
| 6,063,526 A | 5/2000 | Gan et al. | |
| 6,203,949 B1 | 3/2001 | Ehrlich | |
| 6,225,002 B1 | 5/2001 | Nimon et al. | |
| 6,673,273 B2 | 1/2004 | Ba Le et al. | |
| 7,129,005 B2 | 10/2006 | Wensley et al. | |
| 7,422,826 B2 | 9/2008 | King et al. | |
| 8,026,002 B2 | 9/2011 | Rong et al. | |
| 8,227,105 B1 | 7/2012 | Gerald, II et al. | |
| 8,501,339 B2 | 8/2013 | Visco et al. | |
| 8,524,397 B1 | 9/2013 | Yumoto et al. | |
| 2002/0160269 A1* | 10/2002 | Choi ............... | H01M 10/0525 429/303 |
| 2002/0197536 A1 | 12/2002 | Mori et al. | |
| 2003/0104282 A1 | 6/2003 | Xing et al. | |
| 2005/0255385 A1 | 11/2005 | Harrup et al. | |
| 2006/0093921 A1 | 5/2006 | Scott et al. | |
| 2006/0154144 A1 | 7/2006 | Gorkovenko et al. | |
| 2006/0210873 A1 | 9/2006 | Hollenkamp et al. | |
| 2007/0015048 A1 | 1/2007 | Lee et al. | |
| 2007/0054186 A1 | 3/2007 | Costello et al. | |
| 2008/0241665 A1 | 10/2008 | Sano | |
| 2009/0233164 A1 | 9/2009 | Shimamura et al. | |
| 2009/0317725 A1 | 12/2009 | Jiang et al. | |
| 2010/0021815 A1 | 1/2010 | Oh et al. | |
| 2010/0075215 A1 | 3/2010 | Zhang | |
| 2010/0141881 A1 | 6/2010 | Batistatos et al. | |
| 2010/0273062 A1 | 10/2010 | Tsuchida et al. | |
| 2011/0003211 A1 | 1/2011 | Hudson et al. | |
| 2011/0076570 A1 | 3/2011 | Hama et al. | |
| 2012/0107697 A1 | 5/2012 | Roh et al. | |
| 2012/0110835 A1 | 5/2012 | Hudson et al. | |
| 2013/0011728 A1 | 1/2013 | Tokuda et al. | |
| 2013/0011745 A1 | 1/2013 | Johnson et al. | |
| 2013/0019468 A1 | 1/2013 | Ramasubramanian et al. | |
| 2013/0065122 A1 | 3/2013 | Chiang et al. | |
| 2013/0084507 A1* | 4/2013 | Johnson | |
| 2013/0108934 A1* | 5/2013 | Lee ............... | H01M 10/052 429/405 |
| 2013/0134566 A1 | 5/2013 | Ding et al. | |
| 2013/0142943 A1 | 6/2013 | Kubo et al. | |
| 2013/0143134 A1 | 6/2013 | Mizuno et al. | |
| 2013/0189589 A1 | 7/2013 | Hashaikeh et al. | |
| 2013/0330649 A1 | 12/2013 | Takane et al. | |
| 2013/0344367 A1 | 12/2013 | Chiang et al. | |
| 2013/0344397 A1 | 12/2013 | Visco et al. | |
| 2014/0023936 A1 | 1/2014 | Belharouak et al. | |
| 2014/0072881 A1 | 3/2014 | Park | |
| 2014/0287324 A1 | 9/2014 | Tsuchida et al. | |
| 2014/0315097 A1 | 10/2014 | Tan et al. | |
| 2015/0024279 A1 | 1/2015 | Tan et al. | |
| 2015/0047767 A1 | 2/2015 | Sano | |
| 2015/0288028 A1 | 10/2015 | DeSimone et al. | |
| 2016/0146895 A1 | 5/2016 | Yazami | |

FOREIGN PATENT DOCUMENTS

| | | |
|---|---|---|
| CN | 103093965 | 1/2013 |
| EP | 0651455 | 5/1995 |
| EP | 0981175 | 2/2000 |
| EP | 978889 | 8/2001 |
| EP | 1231655 | 8/2002 |
| EP | 2587585 | 5/2013 |
| JP | 11329393 | 11/1999 |
| JP | 2000195494 | 7/2000 |
| JP | 2003242964 | 8/2003 |
| WO | 9202967 | 2/1992 |
| WO | 1999010165 | 3/1999 |
| WO | 1999054953 | 10/1999 |
| WO | 20000038263 | 6/2000 |
| WO | 2001017052 | 3/2001 |
| WO | 2002061872 | 8/2002 |
| WO | 2005043649 | 5/2005 |
| WO | 2008098137 | 8/2008 |
| WO | 2009108185 | 9/2009 |
| WO | 2011014818 | 2/2011 |
| WO | 2011157489 | 12/2011 |
| WO | 2013134566 | 3/2013 |
| WO | 2014020349 | 8/2013 |
| WO | 2013154623 | 10/2013 |

OTHER PUBLICATIONS (PCT/US2015/035918) PCT Notification of Transmittal of the International Search Report and the Written Opinion of the International Searching Authority, dated Oct. 23, 2015, 11 pages.

Henderson, "Cystallization of Kinetics of Glyme-LiX and PEO-LiX Polymer Electrolytes", Macromolecules, 2007, pp. 4963-4971.

Luntz, Alan C. et al., "Interfacial Challenges in Solid-State Li Ion Batteries", Journal of Physical Chemistry, vol. 6, pp. 4599-4604, Nov. 9, 2015.

(PCT/US2015/060515) PCT Notification of Transmittal of the International Search Report and the Written Opinion of the International Searching Authority, dated Feb. 4, 2016, 12 pages.

\* cited by examiner

SEMI-SOLID ELECTROLYTES FOR BATTERIES

BACKGROUND

The disclosure relates to electrolytes for batteries, specifically semi-solid electrolytes for batteries.

Implantable medical devices typically contain a battery as a power source. It is desirable for batteries used in implantable medical devices to have a relatively long battery life. To achieve such relatively long battery life for such batteries, certain battery configurations and chemistries are used. One consideration of designing such batteries is the potential for chemical reduction of electrolyte compositions. Such reduction reactions can result in gas formation within a battery which can over-pressurize certain battery enclosures, such as those having crimp-type seals.

SUMMARY

The electrolytes described in this disclosure are semi-solid and comprise one or more glymes, one or more lithium salts, and one or more polymeric complexing agents, for example polyethylene oxide. The glyme(s) and the lithium salt(s) are present in weight percents or molar ratios based on the total weight or moles of glyme(s) and lithium salt(s). The polymeric complexing agent(s) is present in a weight percent based on the total weight of the semi-solid electrolyte composition.

In one embodiment, an electrolyte composition comprises a glyme or a mixture of glymes (15 to 80 weight percent), a lithium salt, wherein the lithium salt is present in an amount of from 20 to 85 percent by weight based on the total weight of the glyme and lithium salt combined, and a polymeric complexing agent present in an amount of from 5 to 80 percent by weight, based on the total weight of the electrolyte composition, wherein the electrolyte composition is semi-solid.

In another embodiment, an electrolyte composition comprises a glyme or mixture of glymes present in an amount of from about 23 to about 81 mole percent, a lithium salt present in an amount of about 19 to about 77 mole percent, the mole percent based on the total moles of glyme or mixture of glymes and lithium salt, and a polymeric complexing agent present in an amount of from 5 to 80 percent by weight, based on the total weight of the electrolyte composition, wherein the electrolyte composition is semi-solid.

In another embodiment, an electrolyte composition consists essentially of a glyme or a mixture of glymes, a lithium salt, wherein the lithium salt is present in an amount of from 20 to 85 percent by weight based on the total weight of the glyme and lithium salt combined and a polymeric complexing agent present in an amount of from 5 to 80 percent by weight, based on the total weight of the electrolyte composition, wherein the electrolyte composition is semi-solid.

In another embodiment, an electrolyte composition consists essentially of a glyme or mixture of glymes present in an amount of from about 23 to about 81 mole percent, a lithium salt present in an amount of about 19 to about 77 mole percent, the mole percent based on the total moles of glyme or mixture of glymes and lithium salt, and a polymeric complexing agent present in an amount of from 5 to 80 percent by weight, based on the total weight of the electrolyte composition, wherein the electrolyte composition is semi-solid.

In another embodiment, an electrochemical cell comprises a casing, an anode within the casing, a cathode within the casing and any electrolyte composition described or claimed in this application.

DETAILED DESCRIPTION

The electrolyte compositions described in this disclosure are in the form of a semi-solid. As used in this application, "semi-solid" means that the components of the composition are physically cross-linked or physically entangled, chemically cross-linked or chemically bonded, or both, and are gelatinous and not a liquid. The semi-solid electrolyte compositions described in this disclosure typical have a Storage Modulus (1 Hz, 37° C.) of from $10^1$ to $1 \times 10^6$ Pa. In one embodiment, the semi-solid electrolyte compositions are physically cross-linked or physically entangled and not chemically crosslinked.

The semi-solid electrolytes described in this application contain one or more lithium salts or LiX salts. Examples of such LiX salts include lithium bis(trifluoromethylsulfonyl) imide (LiTFSI), lithium bis(pentafluoroethylsulfonyl) imide (LiBETI), lithium tris(trifluorosulfonyl) methide, lithium perchlorate ($LiClO_4$), lithium tetrafluoroborate ($LiBF_4$), lithium hexafluoroarsenate ($LiAsF_6$), lithium hexafluorophosphate ($LiPF_6$) and combinations of any of them.

The semi-solid electrolytes described in this application contain one or more glymes. Examples of useful glymes include tetraethylene glycol dimethyl ether (TEGDME), bis(2-methoxyethyl) ether (Diglyme), triethylene glycol dimethyl ether (Triglyme), poly(ethylene glycol dimethyl ether) (PEGDME) (mw: 200-2000), poly(ethylene glycol)

(mw: 200-2000), polyglycol methyl ether (mw: 200-2000), ethylene glycol dibutyl ether, and combinations of any of them.

The semi-solid electrolytes described in this application contain one or more complexing agents which complexes with the LiX/glyme mixture. A useful polymeric complexing agent is one or more polyethylene oxides (PEO). Examples of useful PEOs are PEOs having a molecular weight of from 100,000 Da to 8,000,000 Da. Specific examples include those having the following CAS # and (molecular weight; Da): 25322-68-3 (100,000); 25322-68-3 (600,000); and 25322-68-3 (5,000,000), available from Sigma-Aldrich.

Other examples of polymeric complexing agents include: copolymers of ethylene oxide with silicone, urethane, styrene, alkyl methacrylate monomers, ethylene oxide grafted onto main chains of phosphazene and silicone polymers, polyacrylonitrile, polyimide, poly methyl methacrylate, poly acrylic acid, and poly lithium acrylate. Further examples of complexing agents include, inorganic particles based on silica, alumina, titania, montmorillonite, hectorite, and zeolites.

The semi-solid electrolytes described in this application do not contain water (are nonaqueous), components or additives that can undergo reduction at potentials between 3V and 0V (vs. $Li^+/Li$), for example propylene carbonate, low molecular weight impurities found in glymes, for example dimethyl ether (DME), or components or additives that possess significantly higher vapor pressure than that of Tetraglyme or any other higher molecular weight or higher boiling point glymes.

The semi-solid electrolyte compositions described in this disclosure are useful in batteries, typically containing an anode, a cathode and a separator enclosed within a casing. Useful materials that can be used in an anode of such a battery include lithium metal, lithium alloys (Li—Al, Li—Si, Li—Sn), graphitic carbon, petroleum coke, MCMB, lithium titanate ($Li_4Ti_5O_{12}$), and combinations of any of them. Useful materials that can be used in a cathode in such a battery include $SVO/CF_x$, $MnO_2/CF_x$, SVO, $MnO_2$, $CF_x$, $LiCoO_2$, $LiMn_2O_4$, $LiNi_{1/3}Mn_{1/3}Co_{1/3}O_2$, $LiNiO_2$, S, and $Li_xS$.

Useful materials for use in or as a separator include microporous materials including cellulose, polypropylene (PP), polyethylene (PE), PP/PE/PP (tri-layer) and microporous membranes, cloths and felts made from ceramic materials such as $Al_2O_3$, $ZrO_2$, and $SiO_2$ based materials that are chemically resistant to degradation from the battery electrolyte. Examples of commercially available microporous materials include Celgard™ 2500, Celgard™ 3501, Celgard™ 2325, Dreamweaver™ Gold, and Dreamweaver™ Silver. Other useful materials include nonwoven PP materials and non-woven PP laminated to microporous separators commercially available as Freudenberg/Viledon™ and Celgard™ 4560 respectively.

Useful casings for the batteries described in this application can be hermetic or semi-hermetic. Examples of hermetic casings include metal cases having a glass-metal feedthrough or a ceramic feedthrough. Examples of semi-hermetic casings include coin cells, laminated metal foil packs, adhesive bonded metal cases, and crimped metal cases.

In general, the electrolyte compositions described in this application are made by first combining the LiX salt with the glyme(s) in a glass container with stirring at room temperature for about 8-12 hours. The resulting mixture is a liquid at 20° C. and 37° C. The LiX/glyme(s) mixture is then mixed with the desired amount of polymer, for example PEO until a uniform mixture is achieved. Mixing of the liquid electrolyte with PEO can be achieved in a variety of equipment: screw extruders, planetary mixers, roller mills, static mixers, etc. Mixing at elevated temperatures enables faster processing/shorter mixing times. For example, a mixture containing equimolar amounts of LiX and glyme(s) complexed with PEO present at 12.5% by weight is a viscous liquid at 20° C. and at 37° C.

The LiX salt(s) is/are present in an amount of from about 20 to about to 85 percent by weight (or weight percent) based on the total weight of the glyme(s) and lithium salt combined. In other embodiments, the LiX salt(s) is/are present in an amount of from about 24 to about 82 percent by weight, from about 46 to about 66 percent by weight, and from about 40 to about 66 percent by weight, based on the total weight of the glyme(s) and lithium salt combined. Applicants intend that the above ranges provide support for any numerical range or numerical amount in weight percent within any of the above ranges.

The glyme(s) is/are present in an amount of from about 15 to about 80 percent by weight based on the total weight of the glyme(s) and lithium salt combined. In other embodiments, the glyme(s) is/are present in an amount of from about 18 to about 76 percent by weight, from about 34 to about 54 percent by weight, and from about 34 to about 60 percent by weight, based on the total weight of the glyme(s) and lithium salt combined. Applicants intend that the above ranges provide support for any numerical range or numerical amount in weight percent within any of the above ranges.

In other embodiments, the LiX salt(s) is/are present in an amount of from about 19 to about 77 mole percent based on the total number of moles of glymes(s) and lithium salt combined. In other embodiments, the LiX salt(s) are present in an amount of from about 35 to about 60 mole percent, and from about 35 to about 50 mole percent. Applicants intend that the above ranges provide support for any numerical range or numerical amount in mole percent within any of the above ranges.

In other embodiments, the glyme(s) is/are present in an amount of from about 23 to about 81 mole percent based on the total number of moles of glymes(s) and lithium salt combined. In other embodiments, the glyme(s) are present in an amount of from about 40 to about 65 mole percent, and from about 50 to about 65 mole percent. Applicants intend that the above ranges provide support for any numerical range or numerical amount in mole percent within any of the above ranges.

The polymeric complexing agent(s) is/are present in an amount of from about 5 to about 80 percent by weight, based on the total weight of the electrolyte composition (LiX+glyme(s)+polymeric complexing agents). In other embodiments, the polymeric complexing agent(s) is/are present in an amount of from about 10 to about 60 percent by weight, from about 10 to about 50 percent by weight, and about 10 to about 30 percent by weight based on the total weight of the electrolyte composition. Applicants intend that the above ranges provide support for any numerical range or numerical amount in weight percent within any of the above ranges.

The semi-solid electrolyte compositions described herein are mixed into cathode and/or anode materials before forming the anode and/or cathode materials into their form (for example sheets, pellets, etc.) for use with a separator(s) in a stack to form a battery. In some case, the separator material is also filled or soaked with the semi-solid electrolyte composition.

Through experimentation, Applicant has discovered that desirable semi-solid electrolyte compositions have at least the following properties:

The electrolyte composition have high ionic conductivity (at least $10^{-4}$ S/cm) at 37° C.;

The electrolyte composition have low volatility; Weight loss using TGA measurements<10% at temperatures up to 200° C.;

The electrolyte compositions have physical forms as semi-solids, which are not necessarily capable of being cast into dimensionally stable, free-standing films. Storage modulus measured at 1 Hz and at 37° C. range: 10 Pa-1,000,000 Pa;

Desirable compositions are typically amorphous that either do not possess crystalline phases or have slow crystallization kinetics;

The compositions are incapable of spontaneous demixing that might result in spinodal decomposition; and The electrolyte composition have a high viscosity to avoid macroscopic flow or creep during battery service life (for example 1-20 years).

Figure 1:
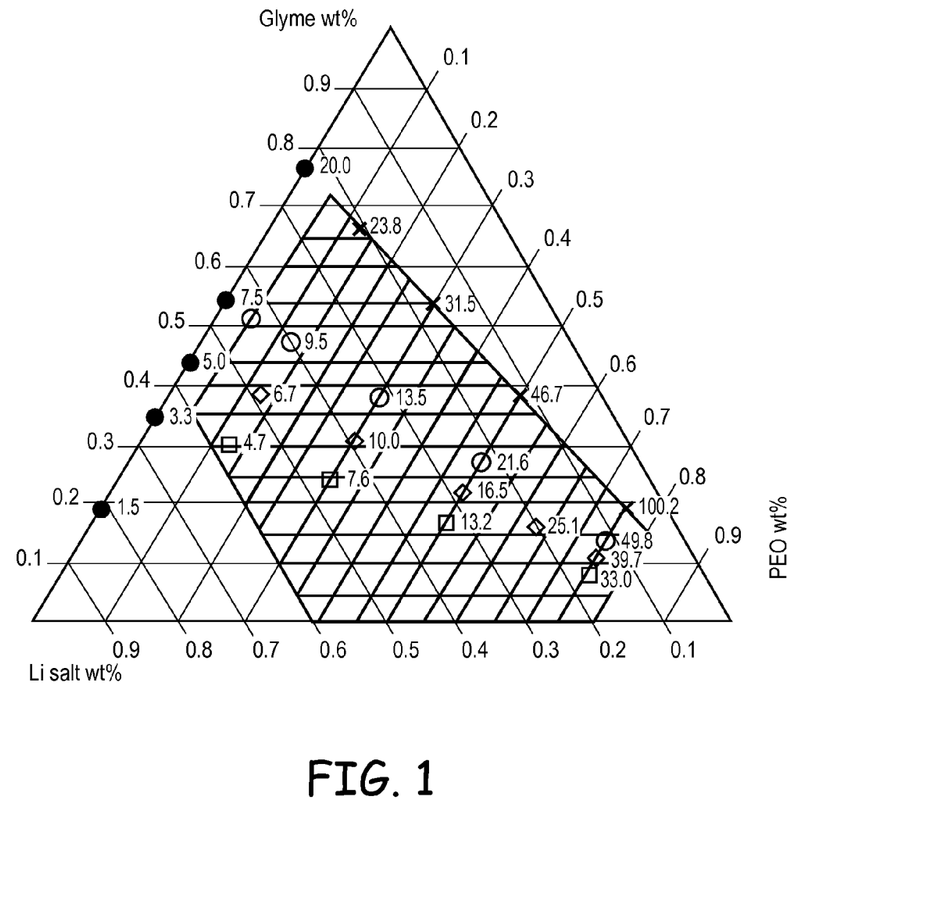
FIG. 1 is a depiction of a ternary diagram of compositions containing a glyme, PEO and a lithium salt.

Experimental:

Table 1 below list various electrolyte compositions tested for ionic conductivity, voltage stability and vapor pressure.

represented on the ternary diagram by symbols. LiTFSI/Tetraglyme compositions are shown on the 0 wt % PEO axis by solid symbols; other compositions were derived from dilution of LiTFSI/Tetraglyme electrolyte solutions with increasing amounts of PEO.

Figure 2A:
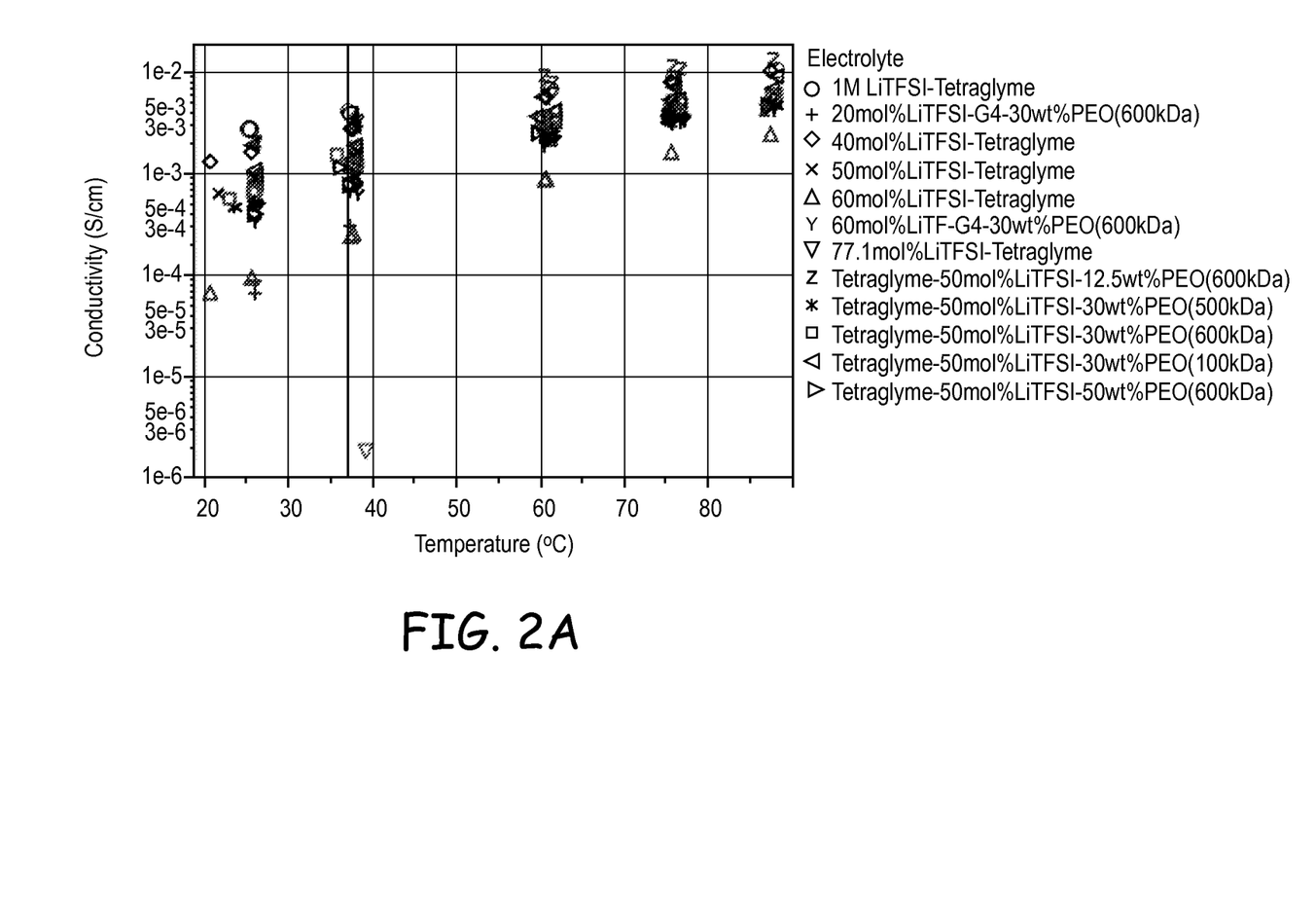
FIGS. 2A and 2B are depictions of plots of Conductivity vs. Temperature of liquid and semi-solid/gel compositions and electrolytes.
Figure 2B:
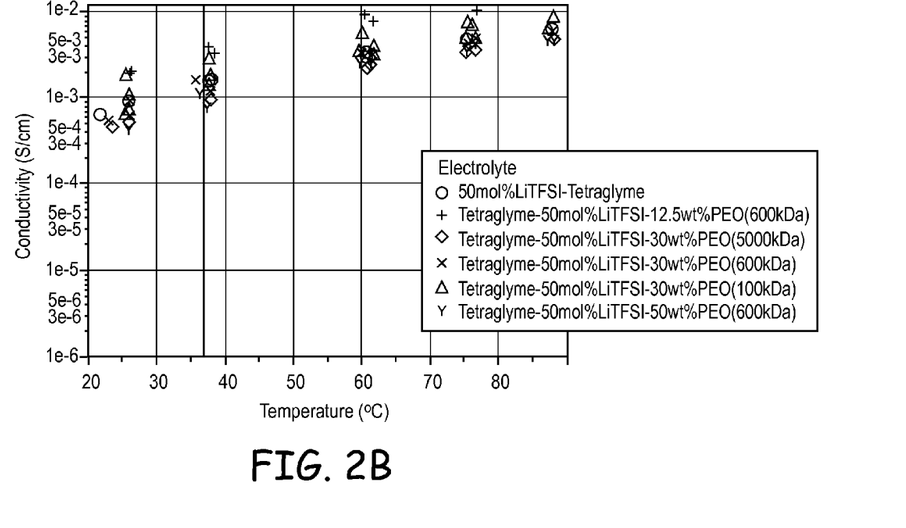
Figure 2C:
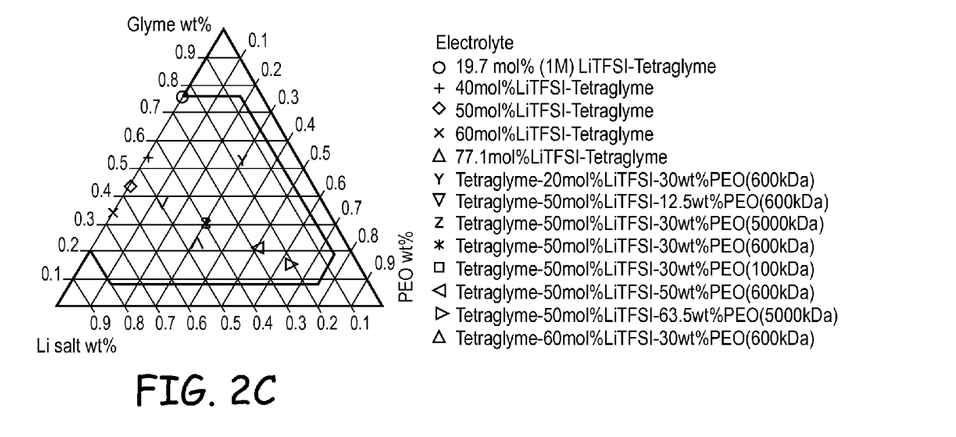
FIG. 2C is a depiction of a ternary plot showing the location of certain compositions and semi-solid electrolytes on such plot.

FIGS. 2A and 2B are plots of Conductivity vs. Temperature of liquid and semi-solid/gel compositions and electrolytes. Such compositions include LiTFSI mixed with Tetraglyme to various molar/weight ratios (Li salt wt. % ranges from 24% to 81%) and subsequently mixed with PEO (12.5 wt % to 63.5 wt % in the final composition) to form semi-solid electrolyte compositions. FIG. 2C shows the location of the compositions and semi-solid electrolyte compositions on a ternary plot.

Figure 3:
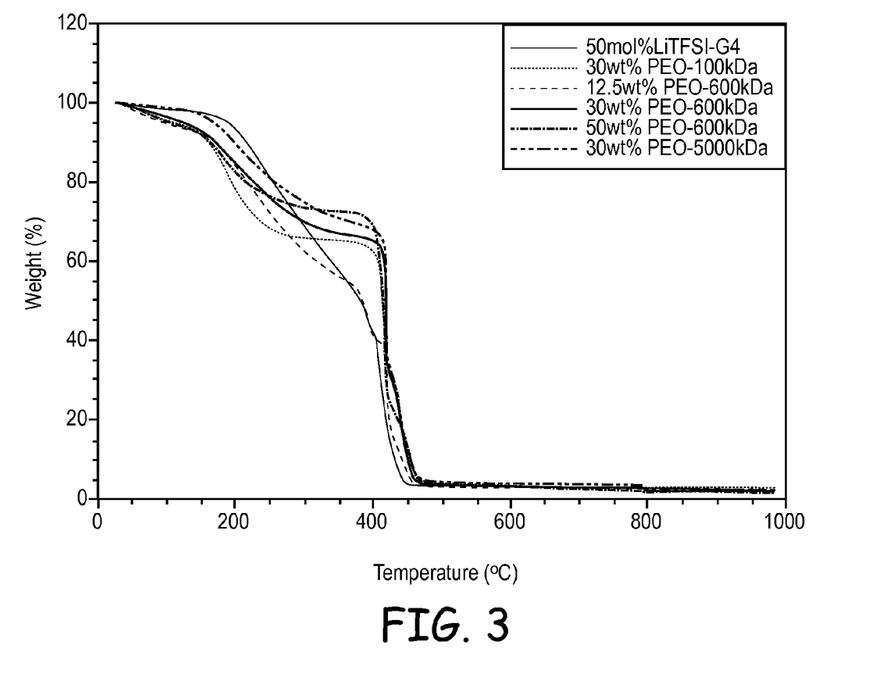
FIG. 3 is a depiction of graphs of thermogravimetric data of compositions containing lithium salt/glyme and lithium salt glyme/PEO.

FIG. 3 shows plots of thermogravimetric data of low volatility liquid compositions (50 mol % LiTFSI/Tetraglyme, ie., 56.36 wt % LiTFSI/Tetraglyme) compared to liquid compositions mixed with PEO of three different molecular weights (100 kDa, 600 kDa, and 5000 kDa) to varying weight ratios (12.5 wt %-50 wt %). The addition of PEO to the liquid compositions does not change the thermal stability or volatility characteristics of the original liquid compositions significantly. In other words, the data show that the low volatility characteristics of the liquid composi-

TABLE 1

| Electrolyte | Li salt | Li salt (wt %) | Li salt (mol %) | Glyme MW (Da) | Glyme (wt %) | Glyme (mol %) | PEO MW (Da) | PEO (wt %) | PEO (mol %) | Conductivity @ 37° C. (S/cm) | EO:Li |
|---|---|---|---|---|---|---|---|---|---|---|---|
| 19.7 mol % (1M) LiTFSI-Tetraglyme | LiTFSI | 24.07% | 19.70% | 222.28 | 75.93% | 80.30% | | | | 4.1E−03 | 20.38 |
| 40 mol % LiTFSI-Tetraglyme | LiTFSI | 46.27% | 40.00% | 222.28 | 53.73% | 60.00% | | | | 2.8E−03 | 7.50 |
| 50 mol % LiTFSI-Tetraglyme | LiTFSI | 56.36% | 50.00% | 222.28 | 43.64% | 50.00% | | | | 1.6E−03 | 5.00 |
| 60 mol % LiTFSI-Tetraglyme | LiTFSI | 65.96% | 60.00% | 222.28 | 34.04% | 40.00% | | | | 2.6E−04 | 3.33 |
| 77.1 mol % LiTFSI-Tetraglyme | LiTFSI | 81.26% | 77.10% | 222.28 | 18.74% | 22.90% | | | | 1.9E−06 | 1.49 |
| PEGDME-500Da-1-6LiTFSI | LiTFSI | 51.99% | 65.35% | 500 | 48.01% | 34.65% | | | | 3.4E−04 | 6 |
| PEGDME-500Da-1-20LiTFSI | LiTFSI | 24.53% | 36.14% | 500 | 75.47% | 63.86% | | | | 1.1E−03 | 20 |
| PEGDME-1000Da-1-10LiTFSI | LiTFSI | 39.43% | 69.40% | 1000 | 60.57% | 30.60% | | | | 2.9E−04 | 10 |
| PEGDME-2000Da-1-6LiTFSI | LiTFSI | 52.07% | 88.33% | 2000 | 47.93% | 11.67% | | | | 6.7E−05 | 6 |
| PEGDME-2000Da-1-20LiTFSI | LiTFSI | 24.58% | 69.42% | 2000 | 75.42% | 30.58% | | | | 6.7E−05 | 20 |
| Tetraglyme-50 mol % LiTFSI-30 wt % PEO (100 kDa) | LiTFSI | 39.45% | 49.95% | 222.28 | 30.55% | 49.95% | 100000 | 30.00% | 0.110% | 2.4E−03 | 10.01 |
| Tetraglyme-50 mol % LiTFSI-12.5 wt % PEO (600 kDa) | LiTFSI | 49.32% | 50.00% | 222.28 | 38.18% | 50.00% | 600000 | 12.50% | 0.006% | 2.3E−03 | 6.64 |
| Tetraglyme-50 mol % LiTFSI-30 wt % PEO (600 kDa) | LiTFSI | 39.45% | 49.99% | 222.28 | 30.55% | 49.99% | 600000 | 30.00% | 0.018% | 1.5E−03 | 9.91 |
| Tetraglyme-50 mol % LiTFSI-50 wt % PEO (600 kDa) | LiTFSI | 28.18% | 49.98% | 222.28 | 21.82% | 49.98% | 600000 | 50.00% | 0.042% | 1.1E−03 | 16.46 |
| Tetraglyme-50 mol % LiTFSI-30 wt % PEO (5000 kDa) | LiTFSI | 39.45% | 50.00% | 222.28 | 30.55% | 50.00% | 5000000 | 30.00% | 0.002% | 9.9E−04 | 9.55 |
| 50 mol % LiAsF6-Triglyme | LiAsF6 | 52.36% | 50.00% | 178.23 | 47.64% | 50.00% | | | | 1.1E−05 | 4.00 |
| 50 mol % LiBF4-Tetraglyme | LiBF4 | 29.66% | 50.00% | 222.28 | 70.34% | 50.00% | | | | 7.8E−04 | 5.00 |
| 67 mol % LiBF4-Tetraglyme | LiBF4 | 46.13% | 67.00% | 222.28 | 53.87% | 33.00% | | | | 1.1E−05 | 2.46 |
| Tetraglyme-50 mol % LiTFSI-63.5 wt % PEO (5000 kDa) | LiTFSI | 20.67% | 50.03% | 222.28 | 15.98% | 49.96% | 5000000 | 63.50% | 0.009% | 2.00E−04 | 25.03 |
| Tetraglyme-20 mol % LiTFSI-30 wt % PEO (600 kDa) | LiTFSI | 17.09% | 20.00% | 222.28 | 52.91% | 79.98% | 600000 | 30.00% | 0.02% | 3.10E−04 | 31.45 |
| Tetraglyme-60 mol % LiTFSI-30 wt % PEO (600 kDa) | LiTFSI | 46.17% | 59.99% | 222.28 | 23.83% | 39.99% | 600000 | 30.00% | 0.02% | 6.80E−04 | 7.57 |

Through experimentation, applicant has discovered that semi-solid electrolyte compositions in the shaded region of the ternary diagram in FIG. 1 are suitable for use in batteries: region of use is bounded by 5%-80% PEO (wt %), 0 wt % glyme, 60 wt % LiTFSI, and a fifth line obtained by diluting 20 mol % LiTFSI/Tetraglyme with increasing amounts of PEO. Labels show the O:Li molar ratio of each composition tions are retained after the addition and complexation of the lithium salt and glyme compositions with PEO.

Figure 4:
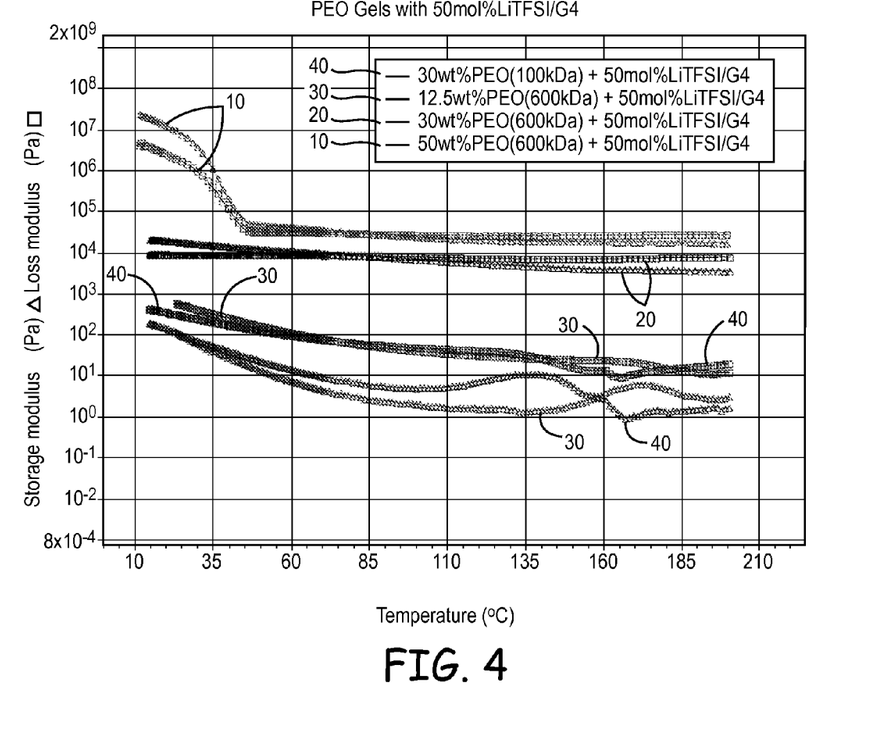
FIG. 4 is a depiction of graphs of Storage and loss moduli of semi-solid electrolyte compositions as a function of temperature at 1 Hz oscillatory strain.

FIG. 4 shows plots of Storage and loss moduli of semi-solid electrolyte compositions as a function of temperature at 1 Hz oscillatory strain. Curves 10 show data for 50 wt % PEO. Curves 20 show data for 30 wt % PEO (600 kDa). Curves 30 show data for 30 wt % PEO (100 kDa). Curves 40 show data for 12.5 wt % PEO. The data show that increased PEO weight percent in the electrolyte compositions results in higher moduli relative to electrolyte compositions s with lower PEO weight percent. Currently, electrolyte compositions with storage moduli between 10 Pa and 1000,000 Pa at 37° C. are preferred.

Figure 5A:
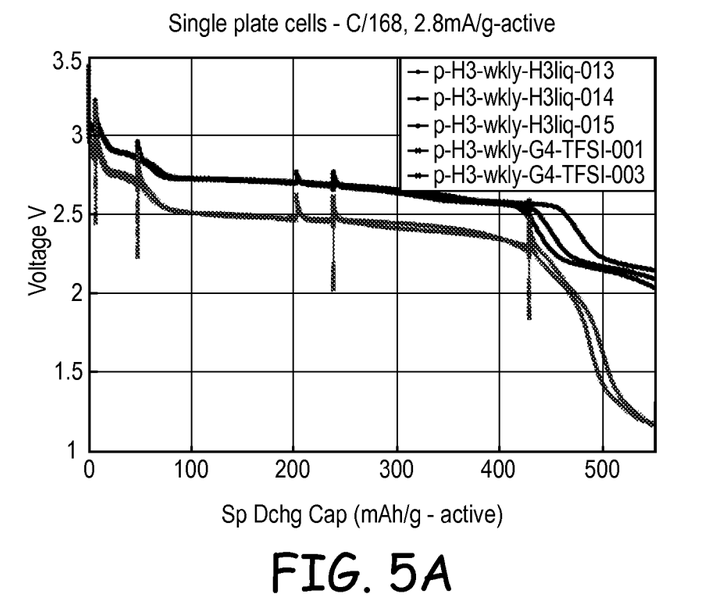
FIG. 5A is a depiction of graphs of the electrical discharge characteristics of a battery having a $CF_x$/SVO cathode and a lithium anode with 50 mol % (56.4 wt %) LiTFSI/Tetraglyme liquid composition) compared to a battery having the same cathode and anode but containing a carbonate-based electrolyte.

FIG. 5A shows plots of the electrical discharge characteristics of a battery having a CFx/SVO cathode and a lithium anode with 50 mol % (56.4 wt %) LiTFSI/Tetraglyme liquid composition (red traces) compared to a battery having the same cathode and anode but containing a carbonate-based electrolyte (1M LiAsF$_6$: propylene carbonate/1,2-dimethoxyethane) (blue traces).

Figure 5B:
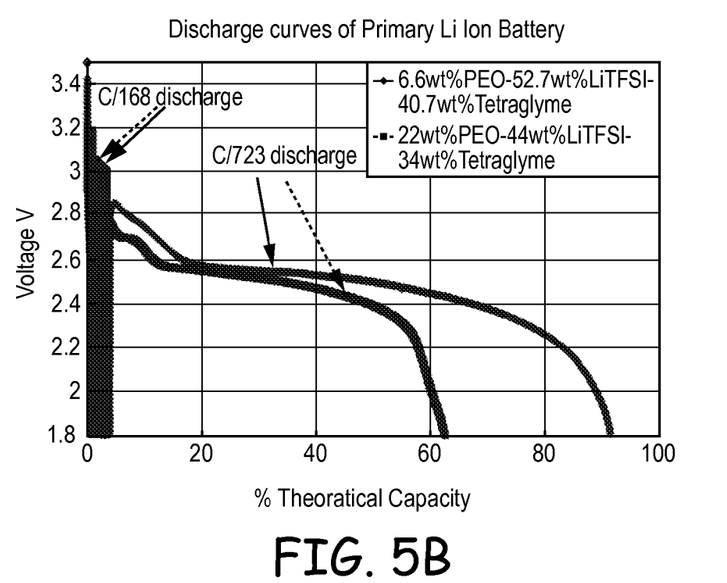
FIG. 5B is a depiction of graphs of the electrical discharge characteristics of batteries having a $CF_x$/SVO cathode and a lithium anode with certain semi-solid electrolyte compositions.

FIG. 5B shows plots of the electrical discharge characteristics of batteries having a CFx/SVO cathode and a lithium anode with semi-solid electrolyte compositions having the following compositions: 6.6 wt % PEO (5000 kDa) complexed with 50 mol % (56.36 wt %) LiTFSI/Tetraglyme; and 22 wt % PEO (5000 kDa) complexed with 50 mol % LiTFSI (56.36 wt %) LiTFSI/Tetraglyme.

Figure 6:
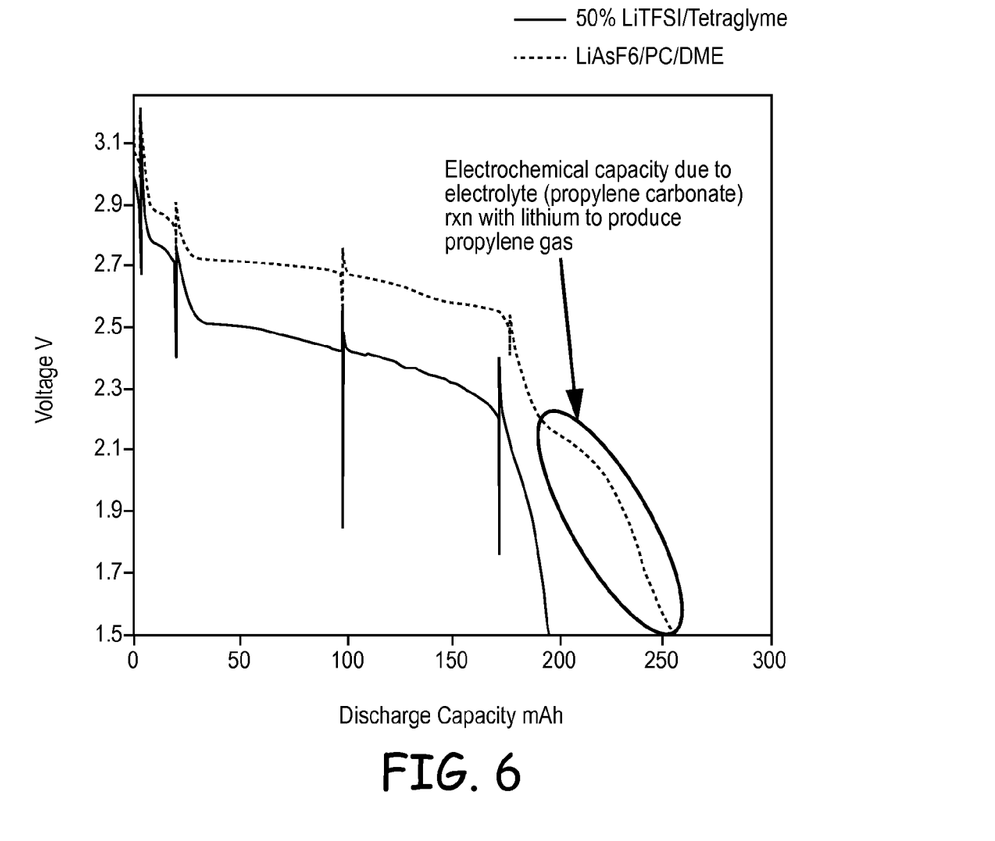
FIG. 6 is a depiction of graphs of Voltage vs. Discharge Capacity for two batteries having a $CF_x$/SVO cathode and a lithium anode, but different compositions of electrolyte.

FIG. 6 shows graphs of Voltage vs. Discharge Capacity for two batteries having a CFx/SVO cathode and a lithium anode, but different compositions of electrolyte. The electrolyte compositions that were compared have the following compositions: (1 M LiAsF$_6$: Propylene carbonate/1,2-dimethoxyethane) (red trace); and 50 mol % (56.36 wt %) LiTFSI/Tetraglyme (blue trace). The data show that the excess electrochemical capacity at voltage<2.4 V (vs. Li+/Li) in the battery containing the electrolyte composition containing propylene carbonate results in gas generation that can cause a battery to swell and potentially rupture. Gas generation was not found in the 50 mol % (56.36 wt %) LiTFSI/Tetraglyme composition at voltages<2.4 V (vs. Li$^+$/Li).

Figure 7:
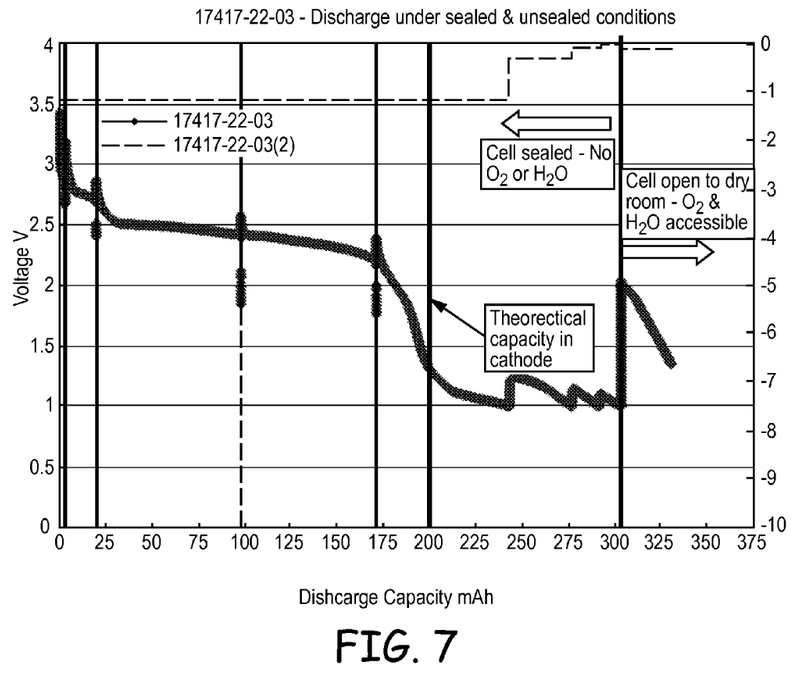
FIG. 7 is a depiction of a graph of Voltage vs. Discharge Capacity for a 3v $CF_x$/SVO cathode and a 2v cathode (oxygen reduction on discharged $CF_x$/SVO cathode).

FIG. 7 shows a graph of Voltage vs. Discharge Capacity for a 3v CFx/SVO cathode and a 2v cathode (oxygen reduction on discharged CF$_x$/SVO cathode). A cell built in an aluminum laminated foil package, contained a CF$_x$/SVO cathode designed with excess capacity in lithium metal anode. Subsequent to the discharge of the CF$_x$/SVO cathode, the cell was cut open, exposed to atmospheric oxygen that was reduced on the carbon that was generated as a result of reduction of CFx using the anode capacity that was in excess to the capacity used by the CFx/SVO cathode and a composition used as an electrolyte containing 50 mol % LiTFSI/Tetraglyme. The data show an approximately 10% extra capacity from discharge in atmospheric oxygen. Such a discharge in atmospheric oxygen would not be possible using an electrolyte containing high dielectric-constant solvents such as propylene carbonate which undergo electrochemical reduction at voltages<2.4 V (vs. Li+/Li).

We claim:

1. A electrolyte composition comprising:
   a glyme or a mixture of glymes, wherein the glyme is tetraethylene glycol dimethyl ether (TEGDME), bis(2-methoxyethyl) ether (Diglyme), triethylene glycol dimethyl ether (Triglyme), poly(ethylene glycol) (mw: 200-2000), polyglycol methyl ether (mw: 200-2000), ethylene glycol dibutyl ether, or combinations of any of them wherein the glyme is present in an amount of from 34 to 54 percent by weight based on the total weight of the glyme and lithium salt combined;
   a lithium salt, wherein the lithium salt is present in an amount of from 40 to 66 percent by weight based on the total weight of the glyme and lithium salt combined; and
   a polymeric complexing agent present in an amount of from 5 to 30 percent by weight, based on the total weight of the electrolyte composition, wherein the electrolyte composition has a storage modulus (1 Hz, 37° C.) of from $10^1$ to $1 \times 10^6$ Pa and has an ionic conductivity of at least $1 \times 10^{-4}$ S/cm at 37° C.

2. The electrolyte composition of claim 1 wherein the polymeric complexing agent is PEO.

3. The electrolyte composition of claim 1 wherein the lithium salt is lithium bis(trifluoromethylsulfonyl) imide (LiTFSI), lithium bis(pentafluoroethylsulfonyl) imide (LiBETI), lithium tris(trifluorosulfonyl) methide, lithium perchlorate (LiClO4), lithium tetrafluoroborate (LiBF4), lithium hexafluoroarsenate (LiAsF6), lithium hexafluorophosphate (LiPF6) or combinations of any of them.

4. The electrolyte composition of claim 1 wherein the polymeric complexing agent is PEO, copolymers of ethylene oxide with silicone, urethane, styrene, alkyl methacrylate monomers, ethylene oxide grafted onto main chains of phosphazene, silicone polymers, polyacrylonitrile, polyimide, poly methyl methacrylate, poly acrylic acid, or poly lithium acrylate.

5. An electrolyte comprising:
   a glyme or mixture of glymes present in an amount of from 40 to 65 mole percent, the mole percent based on the total moles of glyme or mixture of glymes and lithium salt, wherein the glyme is tetraethylene glycol dimethyl ether (TEGDME), bis(2-methoxyethyl) ether (Diglyme), triethylene glycol dimethyl ether (Triglyme), poly(ethylene glycol) (mw: 200-2000), polyglycol methyl ether (mw: 200-2000), ethylene glycol dibutyl ether, or combinations of any of them;
   a lithium salt present in an amount of 35 to 60 mole percent, the mole percent based on the total moles of glyme or mixture of glymes and lithium salt; and
   a polymeric complexing agent present in an amount of from 5 to 30 percent by weight, based on the total weight of the electrolyte composition, wherein the electrolyte composition has a storage modulus (1 Hz, 37° C.) of from $10^1$ to $1 \times 10^6$ Pa and has an ionic conductivity of at least $1 \times 10^{-4}$ S/cm at 37° C.

6. The electrolyte composition of claim 5 wherein the polymeric complexing agent is PEO.

7. The electrolyte composition of claim 5 wherein the lithium salt is lithium bis(trifluoromethylsulfonyl) imide (LiTFSI), lithium bis(pentafluoroethylsulfonyl) imide (LiBETI), lithium tris(trifluorosulfonyl) methide, lithium perchlorate (LiClO4), lithium tetrafluoroborate (LiBF4), lithium hexafluoroarsenate (LiAsF6), lithium hexafluorophosphate (LiPF6) or combinations of any of them.

8. The electrolyte composition of claim 5 wherein the polymeric complexing agent is PEO, copolymers of ethylene oxide with silicone, urethane, styrene, alkyl methacrylate monomers, ethylene oxide grafted onto main chains of phosphazene, silicone polymers, polyacrylonitrile, polyimide, poly methyl methacrylate, poly acrylic acid, or poly lithium acrylate.

9. An electrolyte composition consisting essentially of:
   a glyme or a mixture of glymes them wherein the glyme is present in an amount of from 34 to 54 percent by weight based on the total weight of the glyme and lithium salt combined;
   a lithium salt, wherein the lithium salt is present in an amount of from 40 to 66 percent by weight based on the total weight of the glyme and lithium salt combined; and a polymeric complexing agent present in an amount of from 5 to 30 percent by weight, based on the total weight of the electrolyte composition, wherein the electrolyte composition has a storage modulus (1 Hz, 37° C.) of from $10^1$ to $1 \times 10^6$ Pa and has an ionic conductivity of at least $1 \times 10^{-4}$ S/cm at 37° C.

10. The electrolyte composition of claim 9 wherein the polymeric complexing agent is PEO.

11. An electrochemical cell comprising:
a casing;
an anode within the casing;
a cathode within the casing; and
an electrolyte of claim 1.

12. The electrochemical cell of claim 11 wherein the anode contains a material selected from lithium metal, lithium alloys, graphitic carbon, petroleum coke, lithium titanate or combinations of any of them.

13. The electrochemical cell of claim 11 wherein the cathode contains a material selected from silver vanadium oxide, carbon monofluoride, manganese oxide, $LiCoO_2$, $LiMn_2O_4$, $LiNi_{1/3}Mn_{1/3}Co_{1/3}O_2$, $LiNiO_2$, S, or lithium sulfide.

14. The electrochemical cell of claim 11 wherein the casing is a coin cell, laminated foil pack, an adhesive bonded metal case, or a crimped metal case.

15. The electrochemical cell of claim 11, wherein the casing is hermetic.

16. The electrochemical cell of claim 11, wherein the electrochemical cell is a primary battery.

* * * * *